United States Patent
Moon et al.

(10) Patent No.: US 11,246,882 B2
(45) Date of Patent: Feb. 15, 2022

(54) PHARMACEUTICAL COMPOSITION FOR INHIBITING RESISTANCE AGAINST ANTICANCER DRUGS OF PATIENT SUFFERING FROM OVARIAN CANCER COMPRISING NAG-1 INHIBITOR AS ACTIVE INGREDIENT

(71) Applicant: PUSAN NATIONAL UNIVERSITY INDUSTRY-UNIVERSITY COOPERATION FOUNDATION, Busan (KR)

(72) Inventors: Yuseok Moon, Yangsan-si (KR); Ki Hyung Kim, Busan (KR)

(73) Assignee: PUSAN NATIONAL UNIVERSITY INDUSTRY-UNIVERSITY COOPERATION FOUNDATION, Busan (KR)

(*) Notice: Subject to any disclaimer, the term of this patent is extended or adjusted under 35 U.S.C. 154(b) by 47 days.

(21) Appl. No.: 15/742,525

(22) PCT Filed: Jul. 8, 2016

(86) PCT No.: PCT/KR2016/007421
§ 371 (c)(1),
(2) Date: Jan. 8, 2018

(87) PCT Pub. No.: WO2017/007276
PCT Pub. Date: Jan. 12, 2017

(65) Prior Publication Data
US 2018/0200283 A1    Jul. 19, 2018

(30) Foreign Application Priority Data
Jul. 9, 2015 (KR) ........................ 10-2015-0097690

(51) Int. Cl.
*A61K 31/7105* (2006.01)
*C12Q 1/6886* (2018.01)
*G01N 33/574* (2006.01)
*A61K 31/337* (2006.01)
*A61K 31/713* (2006.01)
*A61K 31/7088* (2006.01)
*G01N 33/50* (2006.01)
*A61K 45/06* (2006.01)
*A61P 35/04* (2006.01)
*A61K 48/00* (2006.01)

(52) U.S. Cl.
CPC ........ *A61K 31/7105* (2013.01); *A61K 31/337* (2013.01); *A61K 31/7088* (2013.01); *A61K 31/713* (2013.01); *A61K 45/06* (2013.01); *A61K 48/005* (2013.01); *A61K 48/0016* (2013.01); *A61P 35/04* (2018.01); *C12Q 1/6886* (2013.01); *G01N 33/5073* (2013.01); *G01N 33/574* (2013.01); *G01N 33/57449* (2013.01); *C12Q 2600/106* (2013.01); *C12Q 2600/158* (2013.01); *G01N 2800/52* (2013.01); *G01N 2800/7028* (2013.01)

(58) Field of Classification Search
None
See application file for complete search history.

(56) References Cited

U.S. PATENT DOCUMENTS

| | | | |
|---|---|---|---|
| 2013/0142784 A1 | 6/2013 | Raychaudhuri et al. | |
| 2015/0056199 A1* | 2/2015 | Kumar | C07K 14/71 424/134.1 |
| 2015/0297577 A1* | 10/2015 | Buckanovich | A61K 31/136 514/300 |

FOREIGN PATENT DOCUMENTS

| KR | 10-2011-0085318 A | 7/2011 |
|---|---|---|
| KR | 10-1191616 B1 | 10/2012 |
| WO | 2011-127297 A1 | 10/2011 |

OTHER PUBLICATIONS

BAM80690 (Sequence Alignment of SEQ ID No. 1 with BAM80690. May 23, 2013. Search conducted on Jan. 6, 2021, 2 pages. (Year: 2013).*
Barezi, S. et al., "The effect of full length and mature NAG-1 protein overexpression on cytotoxicity of celecoxib, tamoxifen and doxorubicin in HT1080", DARU Journal of Pharmaceutical Sciences, 2010, vol. 18, No. 3, pp. 163-167.
Kim, Jong-Sik et al., "The conventional nonsteroidal anti-inflammatory drug sulindac sulfide arrests ovarian cancer cell growth via the expression of NAG-1/MIC-1/GDF-15", Molecular Cancer Therapeutics, Mar. 2005, vol. 4, No. 3, pp. 487-493.

* cited by examiner

*Primary Examiner* — Channing S Mahatan
(74) *Attorney, Agent, or Firm* — Revolution IP, PLLC

(57) ABSTRACT

A pharmaceutical composition includes an NAG-1 inhibitor as an active ingredient for inhibiting resistance against an anticancer drug of an ovarian cancer patient and a method of diagnosing prognosis of resistance against an anticancer drug of an ovarian cancer patient by using the NAG-1 inhibitor. It is found by controlling NAG-1 protein that NAG-1, which is overexpressed in an ovarian cancer patient and in an ovarian cancer stem cell having resistance against an anticancer drug, plays a key role in a chronic inflammatory reaction and resistance against an anticancer drug, and in this regard, NAG-1 can be used as a target gene for effective tumor therapy.

3 Claims, 5 Drawing Sheets
Specification includes a Sequence Listing.

[FIG. 1]
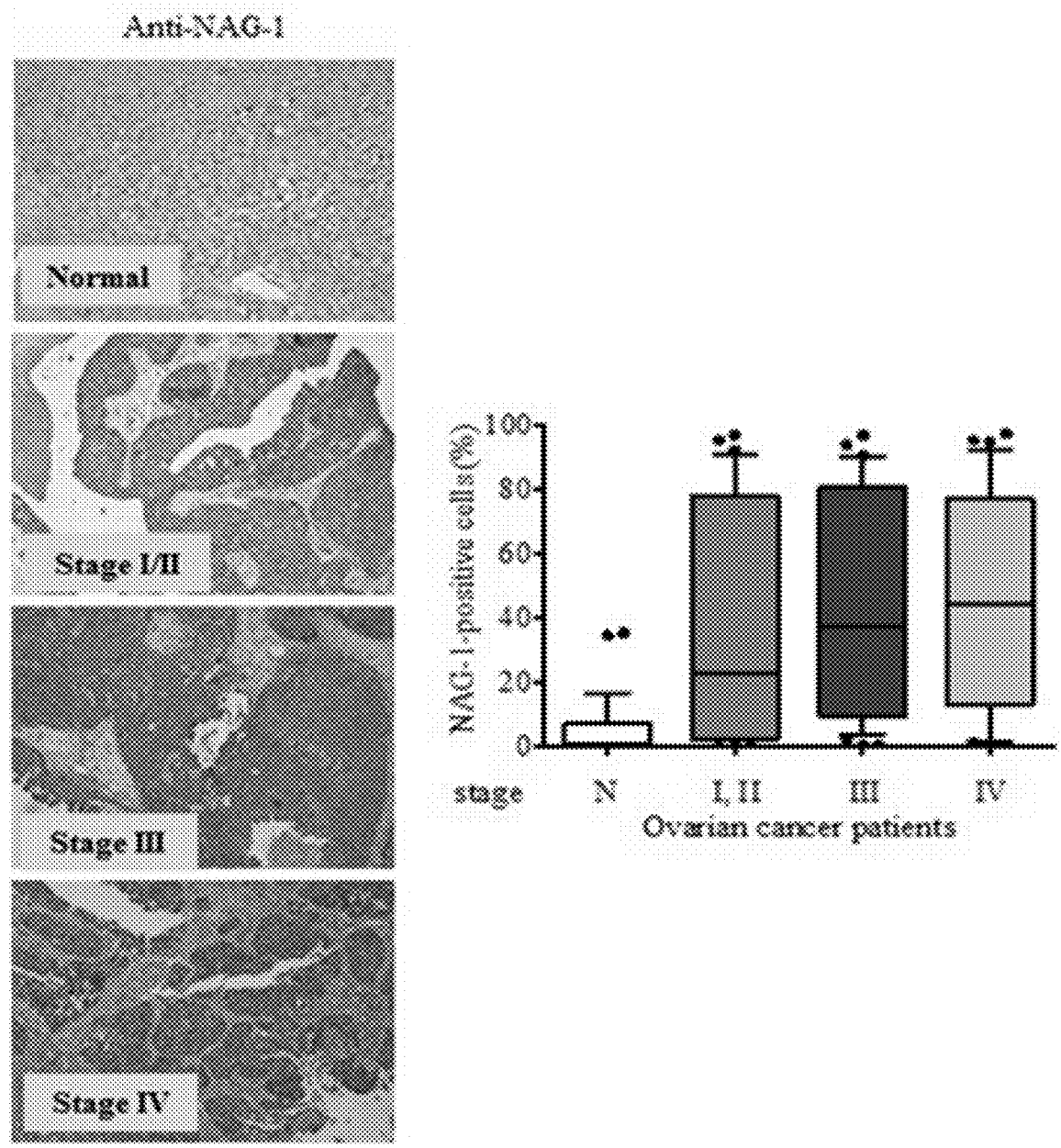

[FIG. 2]
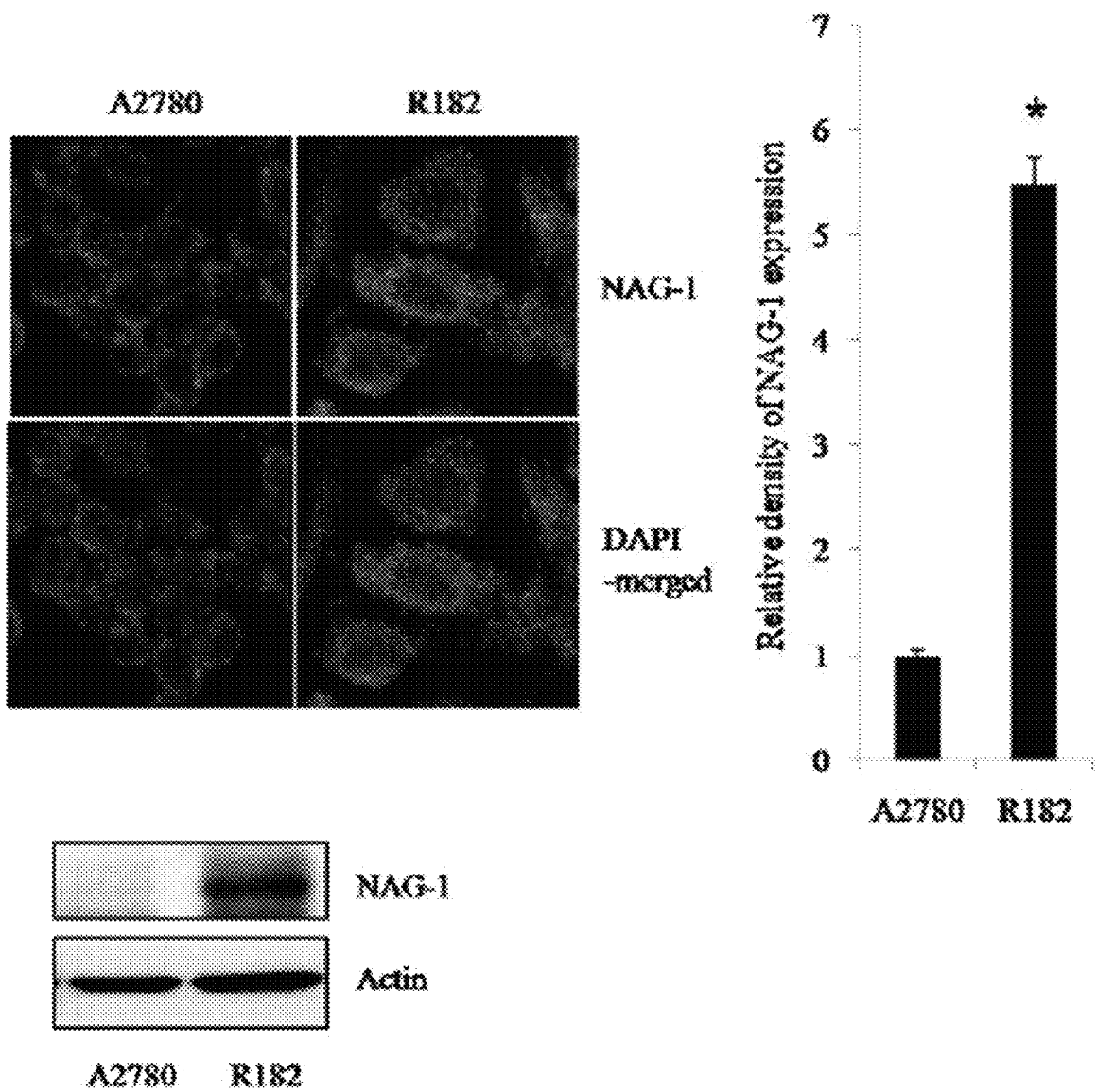

[FIG. 3]
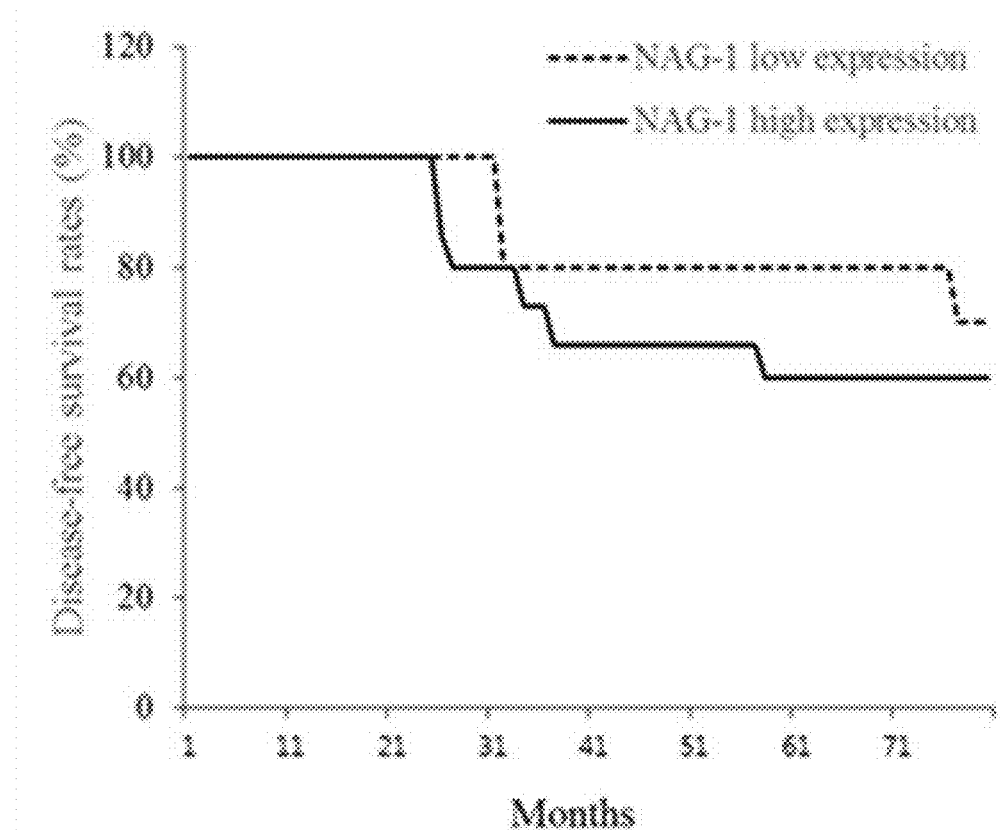
[FIG. 4]
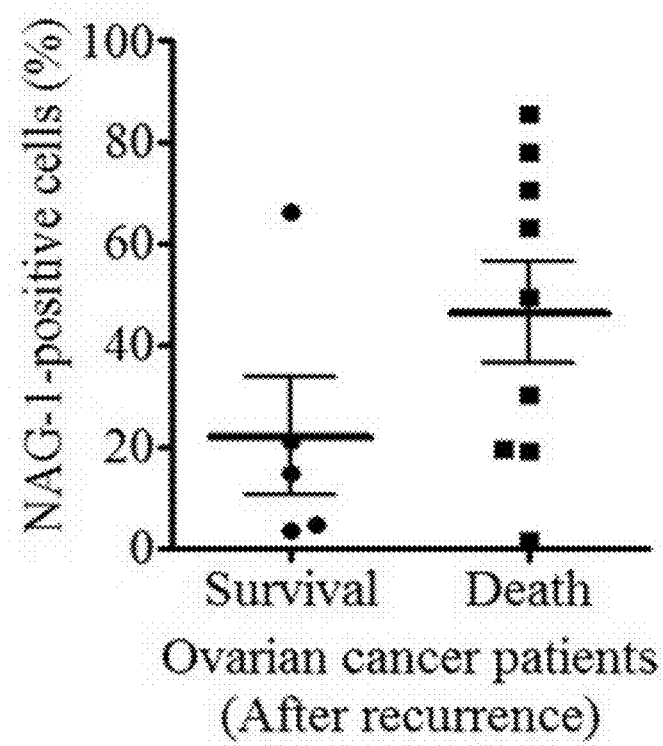

[FIG. 5]
A
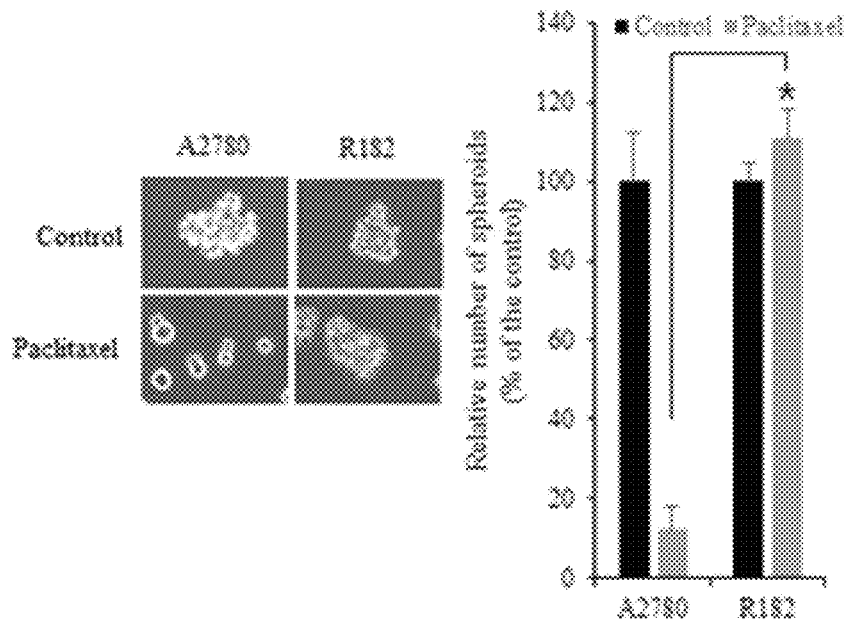
B
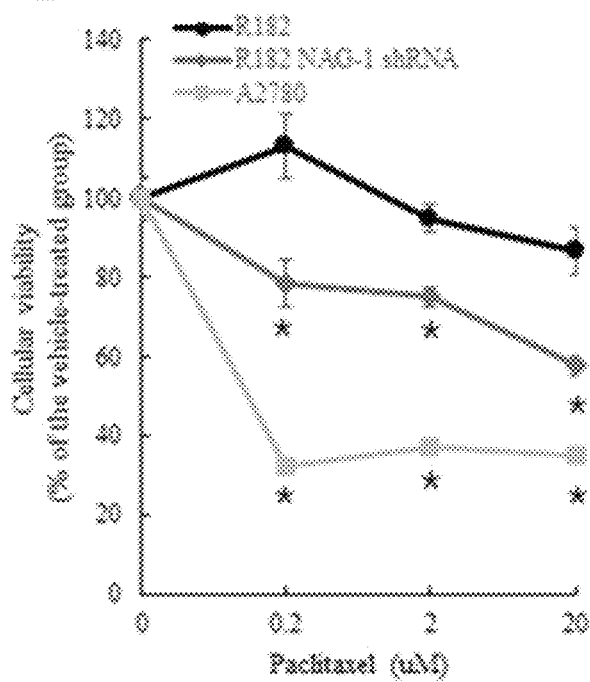
C
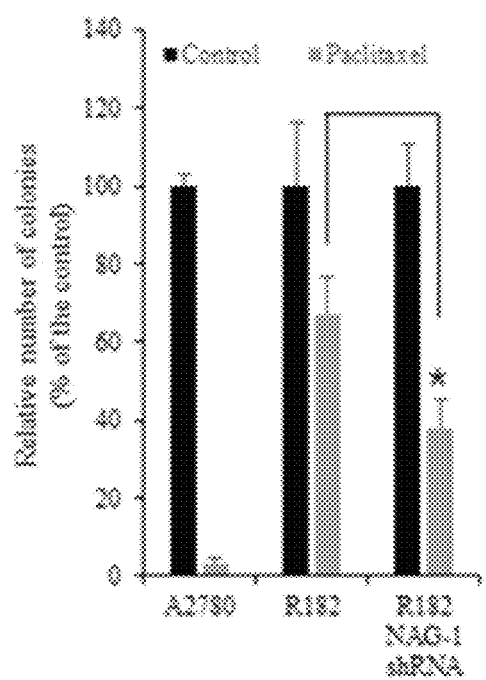

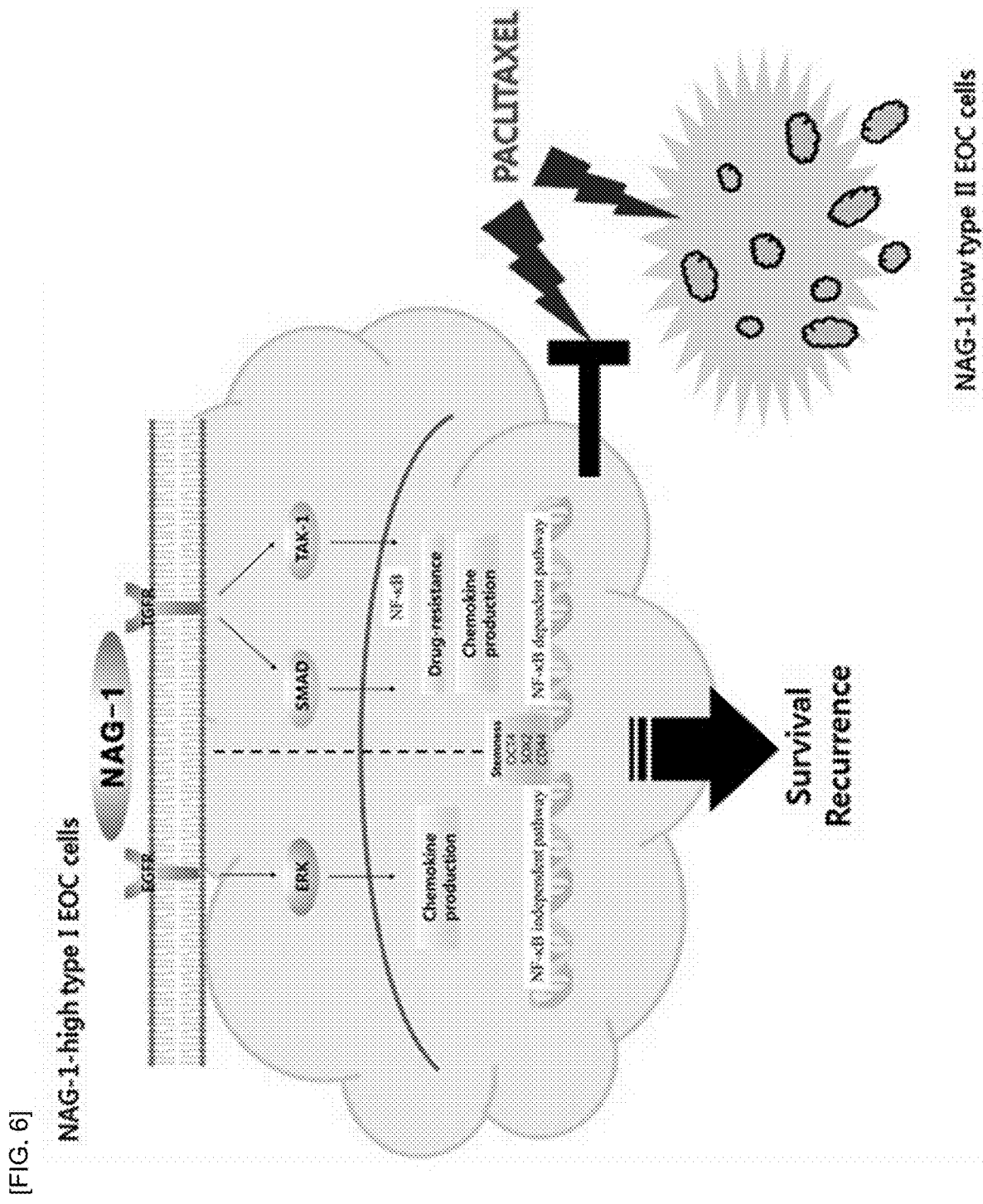
[FIG. 6]

SEQUENCE LISTING

```
<160> NUMBER OF SEQ ID NOS: 1

<210> SEQ ID NO 1
<211> LENGTH: 19
<212> TYPE: RNA
<213> ORGANISM: Artificial Sequence
<220> FEATURE:
```

```
<223> OTHER INFORMATION: shRNA

<400> SEQUENCE: 1
acaugcacgc gcagaucaa                                                  19
```

PHARMACEUTICAL COMPOSITION FOR INHIBITING RESISTANCE AGAINST ANTICANCER DRUGS OF PATIENT SUFFERING FROM OVARIAN CANCER COMPRISING NAG-1 INHIBITOR AS ACTIVE INGREDIENT

TECHNICAL FIELD

The present invention relates to a pharmaceutical composition including an NAG-1 inhibitor as an active ingredient for inhibiting resistance against an anticancer drug of an ovarian cancer patient and a method of diagnosing prognosis of resistance against an anticancer drug of an ovarian cancer patient by using the NAG-1 inhibitor.

BACKGROUND ART

In the United States, ovarian cancer is one of the major causes of female cancer death, and chronic inflammation is considered as an important risk factor for ovarian endometriosis that can progress to epithelial ovarian cancer. Due to no symptoms in early stages of ovarian cancer and a lack of effective early diagnostic techniques, ovarian cancer generally progresses to a more advanced stage. All stages of ovarian cancer development, including tumor production, promotion, and progression, are closely related to inflammatory response. A recent study has shown that epithelial ovarian cancer cells, which express myeloid differentiation protein 88 (MyD88), continuously activate NF-κB and produce a cytokine causing chemical resistance against paclitaxel.

Through several epidemiological studies, non-steroidal anti-inflammatory drugs (NSAIDs) are known to be involved in reducing the risk of progression of a variety of cancers including ovarian cancer. In addition, in many cancer cell lines, NSAID has been shown to induce expression of NSAID-activated protein 1 (NAG-1). NAG-1 is also known as macrophage inhibitory cytokine 1 (MIC-1), growth differentiation factor 15 (GDF15), prostate-derived factor (PDF), placental bone morphogenetic protein (PLAB), and placental transforming growth factor-β (PTGF-β).

In most cases, intestinal epithelial NAG-1 is expressed at a low level, but expression thereof can be induced at a relatively high level under abnormal conditions such as wounds, tumors, and inflammation. In this regard, NAG-1 is expressed at a high level in a cancer patient having prostate cancer, colon cancer, breast cancer, and the like. In the case of human epithelial cancer, an increased level of NAG-1 in serum is related to progression of tumor through metastasis, and thus, NAG-1 in serum can be clinically used for diagnosis and prediction of chronic inflammation and a cancer disease. However, the relationship between the expression of NAG-1 and antibiotic resistance is not clearly identified yet.

DETAILED DESCRIPTION OF THE INVENTION

Technical Problem

The present invention provides a pharmaceutical composition for inhibiting resistance against an anticancer drug, the pharmaceutical composition including, as an active ingredient, an inhibitor of expression or activity of NAG-1 protein.

In addition, the present invention provides a method of diagnosing prognosis of resistance against an anticancer drug of an ovarian cancer patient by using the inhibitor of expression or activity of NAG-1 protein.

In addition, the present invention provides a method of screening an inhibitor of an anticancer drug resistance in an ovarian cancer patient by using NAG-1 protein.

Technical Solution

The present invention provides a pharmaceutical composition for inhibiting resistance against anticancer drug of an ovarian cancer patient, the pharmaceutical composition including, as an active ingredient, an inhibitor of expression or activity of NAG-1 protein.

In addition, the present invention provides a method of providing information for diagnosis of prognosis of resistance against an anticancer drug of an ovarian cancer patient, the method including: treating an ovarian cancer stem cell line with an inhibitor of expression or activity of NAG-1 protein; measuring a level of expression or activity of NAG-1 protein in the treated ovarian cancer stem cell line; comparing the measured level of expression or activity of NAG-1 protein with a control sample; and determining inhibition of resistance against the anticancer drug, when the measured level of expression or activity of NAG-1 protein is lower than that of the control group.

In addition, the present invention provides a method of screening an inhibitor of resistance against an anticancer drug of an ovarian cancer patient, the method including: contacting an ovarian cancer stem cell line with a test substance; measuring a level of expression or activity of NAG-1 protein in the ovarian cancer stem line in contact with the test substance; and screening the test substance having a reduced level of expression or activity of NAG-1 protein by comparing with a control sample.

Advantageous Effects of the Invention

The present invention relates to a pharmaceutical composition including an NAG-1 inhibitor as an active ingredient for inhibiting resistance against an anticancer drug of an ovarian cancer patient and a method of diagnosing prognosis of resistance against an anticancer drug of an ovarian cancer patient by using the NAG-1 inhibitor. It is found by controlling NAG-1 protein that NAG-1, which is overexpressed in an ovarian cancer patient and in an ovarian cancer stem cell having resistance against an anticancer drug, plays a key role in a chronic inflammatory reaction and resistance against an anticancer drug, and in this regard, NAG-1 can be used as a target gene for effective tumor therapy.

DESCRIPTION OF THE DRAWINGS

FIG. 1 shows expression levels of NAG-1 in a normal tissue and in a tissue of an ovarian cancer patient, wherein anti-NAG-1 Ab staining results obtained by immunoperoxydase assay are shown on the left and NAG-1 DAB staining results measured using the Histo-quest tissue analysis software are shown on the right.

FIG. 2 shows expression levels of normal ovarian cancer cells (A2780) and cells of NAG-1 in an ovarian cancer stem cell line (R182), wherein A2780 cells and R182 cells were stained with an anti-NAG-1 Ab and DAPI before being analyzed by confocal microscopy (original magnification× 1,800) (top left), the NAG-1 expression levels are compared with quantitative values (top right), and * indicates similarity between two groups (p<0.05), and results obtained by western blot analysis on cellular lysates of A2780 cells and R182 cells are shown on the bottom.

FIG. 3 shows analysis results on survival rates according to NAG-1 expression in a tissue of an ovarian cancer patient.

FIG. 4 shows analysis results on survival rates according to NAG-1 expression in a tissue of a patient having ovarian cancer recurrence.

FIG. 5 shows effects of controlling NAG-1 in an ovarian cancer cell line in reducing resistance against an anticancer drug, Taxol.

FIG. 6 is a schematic diagram showing resistance controlled by NAG-1 against an anti-inflammatory drug and an anticancer drug.

BEST MODE

The present invention provides a pharmaceutical composition for inhibiting resistance against an anticancer drug of an ovarian cancer patient, the pharmaceutical composition including, as an active ingredient, an inhibitor of expression or activity of NAG-1 protein. Preferably, the anticancer drug may be Taxol, but is not limited thereto.

Preferably, the inhibitor of expression of NAG-1 protein may be an antisense nucleotide binding complementarily to mRNA of NAG-1 gene, a small interfering RNA (siRNA), or a short hairpin RNA (shRNA), and more preferably, the shRNA may consist of SEQ ID NO: 1, but is not limited thereto.

Preferably, the inhibitor of activity of NAG-1 protein may be a compound, a peptide, a peptide mimetic, an aptamer, an antibody, or a natural ingredient, which specifically binds to NAG-1 protein, but is not limited thereto.

Preferably, the NAG-1 protein may be derived from all eukaryotes including mammals, such as humans, cows, goats, sheep, pigs, mice, and rabbits, and having NAG-1. In an embodiment of the present invention, a protein having NCBI accession no. NM_004864 is used as a target protein, but is not limited thereto.

The term "antisense nucleotide" as used herein refers to DNA or RNA, or a derivative thereof, having a nucleic acid sequence complementary to a sequence of specific mRNA. The antisense nucleotide binds to a complementary sequence in mRNA to thereby inhibit translation of mRNA into protein.

The term "small interfering RNA (siRNA)" as used herein refers to a nucleic acid molecule capable of mediating RNA inference or gene silencing. Since the siRNA can inhibit expression of a target gene, the siRNA is provided as an effective gene knockdown method or as a gene therapy method.

The term "short hairpin RNA (shRNA)" as used herein is prepared as follows: an oligodeoxynucleotide connecting 3 to 10 base linkers between a sense of siRNA sequence of target gene and a nonsense complementary thereto is synthesized; the synthesized oligodeoxynucleotide is cloned into a plasmid vector or a shRNA is inserted into a retrovirus, e.g., lentivirus and adenovirus, for expression; once expressed, a short hairpin RNA which is hairpin-structured and has a loop is resulted; and the resulted shRNA is converted into a siRNA by intracellular dicer, thereby exhibiting an RNAi effect. The shRNA exhibits a relatively long-term RNAi effect as compared to the siRNA.

The term "peptide mimetic" as used herein refers to a peptide or a nonpeptide that inhibits a binding domain of the NAG-1 protein which leads the NAG-1 activity.

The term "aptamer" as used herein refers to a single stranded nucleic acid (e.g., DNA, RNA, or modified nucleic acid) having a stable tertiary structure and high affinity and specificity to a target molecule. The aptamer is comparable with a monoclonal antibody due to high affinity (pM levels in usual) and specificity to a target molecule. In particular, the aptamer has high possibility as an alternative antibody to such an extent as to be called as a "chemo-antibody".

The term "antibody" as used herein may be prepared by injection of NAG-1 or may be purchased from the market. In addition, the antibody may include a polyclonal antibody, a monoclonal antibody, and a fragment capable of binding an epitope.

A polyclonal antibody can be prepared according to a conventional method that the NAG-1 is injected into an animal and blood is collected from the animal to obtain serum containing an antibody. Such a polyclonal antibody can be purified by any method known in the art, and can be prepared from any animal species host, such as goat, rabbit, sheep, monkey, horse, pig, cow, dog, and the like. A monoclonal antibody can be prepared using any technique that provides production of an antibody molecule through continuous culturing of a cell line. Such a technique is not limited thereto, and may include a hybridoma technique, a human B-cell line hybridoma technique, and a EBV-hybridoma technique.

The pharmaceutical composition according to the present invention may include, as an active ingredient, a chemical substance, a nucleotide, an antisense, a siRNA oligonucleotide, and a natural extract. The pharmaceutical composition according to the present invention or a complex medication may be prepared using a pharmaceutically acceptable adjuvant in addition to the active ingredient. For use as the adjuvant, a solubilizer, such as an excipient, a disintegrating agent, a sweetener, a binder, a coating agent, a swelling agent, a lubricant, a glydent, or a flavoring agent, may be used. Regarding administration, the pharmaceutical composition according to the present invention may further include at least one pharmaceutically acceptable carrier in addition to the active ingredient, so as to be preferably formulated into a pharmaceutical composition. As an acceptable pharmaceutical carrier for a composition that is formulated into a liquid solution, saline solution, sterile water, Ringer's solution, buffer saline, albumin injection solution, dextrose solution, maltodextrin solution, glycerol, and ethanol may be mixed with at least one of these components, wherein these components are sterilized and suitable for the living body. If necessary, other additives, such as an antioxidant, a buffer solution, and a bacteriostatic agent, may be added. In addition, a diluent, a dispersant, a surfactant, a binder, and a lubricant may be further added to the pharmaceutical composition, so as to be formulated into an injectable formulation, such as an aqueous solution, a suspension, and an emulsion, a pill, a capsule, a granule, or a tablet.

A pharmaceutical dosage form of the pharmaceutical composition of the present invention may be granule, powder, coated tablet, tablet, capsule, suppository, syrup, juice, suspension, emulsion, drop or injectable solution, or sustained release form of an active compound. The pharmaceutical composition of the present invention may be administered in a conventional manner via intravenous, intraarterial, intraperitoneal, intramuscular, intrasternal, percutaneous, nasal, inhalation, topical, rectal, oral, intraocular, or intradermal route. An effective amount of the active ingredient of the pharmaceutical composition of the present invention refers an amount required for prevention or treatment of a disease, and thus, may be adjusted according to various factors, such as type of disease, severity of disease, type and amount of the active ingredient and other ingredients contained in the composition, type of formulation, age, weight, general health condition, and gender of a patient, diet, time of administration, route of administration, secretion rate of the composition, treatment duration, and drug that is used simultaneously. Although not limited thereto, for example, in the case of an adult under conditions where administration is made once to several times a day, a 0.1 ng/kg~10 g/kg of the inhibitor of the present invention may be administered in the case of a compound, 0.1 ng/kg~10 g/kg of the inhibitor of the present invention may be administered in the case of polypeptide, protein, or antibody, and 0.01 ng/kg~10 g/kg of the inhibitor of the present invention may be administered in the case of antisense nucleotide, siRNA, shRNAi, or miRNA, when administered once to several times a day.

In addition, the present invention provides a method of providing information for diagnosis of prognosis of resistance against an anticancer drug of an ovarian cancer patient, the method including: treating an ovarian cancer stem cell line with an inhibitor of expression or activity of NAG-1 protein; measuring a level of expression or activity of NAG-1 protein in the treated ovarian cancer stem cell line; comparing the measured level of expression or activity of NAG-1 protein with a control sample; and determining inhibition of resistance against the anticancer drug, when the measured level of expression or activity of NAG-1 protein is lower than that of the control group.

Preferably, the anticancer drug may be Taxol, but is not limited thereto. Preferably, the inhibitor of expression or activity of NAG-1 protein may be shRNA having SEQ ID NO: 1 (ACAUGCACGCGCAGAUCAA), but is not limited thereto.

In detail, a level of expression or activity of NAG-1 protein may be measured by reverse transcription-polymerase chain reaction (RT-PCR), enzyme-linked immunosorbent assay (ELISA), immunohistochemistry, western blotting, or fluorescence-activated cell sorting (FACS), but is not limited thereto.

In addition, the present invention provides a method of screening an inhibitor of resistance against an anticancer drug of an ovarian cancer patient, the method including: contacting an ovarian cancer stem cell line with a test substance; measuring a level of expression or activity of NAG-1 protein in the ovarian cancer stem line in contact with the test substance; and screening the test substance having a reduced level of expression or activity of NAG-1 protein by comparing with a control sample. Preferably, the anticancer drug may be Taxol, but is not limited thereto.

The term "test substance" as used herein in connection with the method of screening of the present invention refers to an unknown candidate substance used in screening to examine whether such a test substance influences the gene expression amount or the protein expression or activity. The sample may be a chemical substance, a nucleotide, an antisense-RNA, siRNA, and a natural extract, but is not limited thereto.

The term "diagnosis" as used herein refers to identification of the presence or characteristics of pathological conditions. In the present invention, the diagnosis refers to identification of the presence of inhibition of resistance against an anticancer drug of an ovarian cancer patient.

MODE OF THE INVENTION

Hereinafter, the present invention will be described in detail with reference to examples for the purpose of facilitating understanding of the present invention. However, embodiments described below are intended to exemplify the main concepts of embodiments and not limit embodiments. These embodiments are provided so that this disclosure will be thorough and complete, and will fully convey the concept of embodiments to those skilled in the art.

<Experimental Examples>

The following experimental examples are intended to provide experimental examples that are commonly applied to the respective embodiments according to the present invention.

1. Cell Culture and Reagents

Human epithelial ovarian cancer stem cell line R182 cells were provided by Prof. Gil Mor (Yale University School of Medicine). A2780 cells were purchased from American Type Culture Collection (Manassas, Va.). Cells were maintained in RPMI 1640 medium (supplemented with 20% [v/v] heat-inactivated FBS, 50 U/ml penicillin, and 50 mg/ml streptomycin) in a 5% $CO_2$ humidified incubator at 37° C. Cell numbers were counted by trypan blue (Sigma-Aldrich, St. Louis, Mo., USA) using a hemocytometer according to dye exclusion assay.

2. Patient and Sample Preparation

Ovarian cancer tissue samples were collected from ovarian cancer patients with stage III/IV. All patients signed consent forms, and the use of patient samples was approved by the institutional review board of Pusan National University Hospital (PNUH #1007-006-001, PNUH #1007-007-001).

3. Plasmid Preparation

SMAD4 shRNA was obtained from Addgene (Cambridge, Mass., USA). An NAG-1 shRNA expression vector was provided by Jong-Sik Kim (Andong National University, South Korea) and Seong-Joon Baek (University of Tennessee, Tenn., USA).

4. Western Immunoblot Analysis

Cells were washed with a phosphate buffer solution, lysed with in a cell lysis buffer solution containing sodium dodecyl sulfate (SDS), 1.0 mM sodium orthovanadate, and 10 mM Tris (pH 7.4), and then, sonicated for 5 seconds. The supernatant was collected by a centrifuge at 12,000 rpm for 10 minutes 4° C., and then, quantified using a BCA protein assay kit (Welgene, South Korea). A total of 30 ug of proteins was separated using 10% SDS-polyacrylamide mini gels (Bio-Rad, Hercules, Calif., USA). Proteins on the gels were transferred onto polyvinylidene fluoride membranes (Amersham Pharmacia Biotech, Piscataway, N.J., USA), and the membranes blocked non-specific responses to antibodies by using 5% skim milk containing a Tris-buffered solution and Tween 0.05% (Tris-buffered saline plus Tween 0.05%; TBST). Protein bands were probed with anti-NAG-1 primary antibodies (Santa Cruz, Calif., USA), and then, horseradish peroxidase-conjugated anti-goat secondary antibodies (Santa Cruz) were used. According to the manufacturer's instructions, the protein bands were visualized by enhanced chemiluminescence.

5. Immunohistological Measurement

Formalin-fixed paraffin-embedded tissues were cut from human ovaries, deparaffinized, and returned to the original state. For antigen retrieval, the tissue sections were heated in 10 mM sodium acetate (pH 9.0) for 5 minutes at a temperature of 121° C. To remove endogenous peroxidase, tissues were batched in a 3% $H_2O_2$-PBS solution for 15 minutes at room temperature in the dark. After samples were washed with Tris-HCl-Tween 0.5%, and blocked with 3% bovine serum albumin (BSA) in PBS for 1 hour, and incubated at a temperature 4° C. overnight for a reaction with primary antibodies (1:200 dilution). After washing with PBS three times, samples were incubated for 2 hours for a reaction with the horseradish peroxidase-conjugated secondary antibodies, and then, were washed with PBS three times. The bound antibodies were identified using a fresh substrate buffer solution (0.05% diaminobenzidine (DAB, Sigma-Aldrich Chemical Co.) and 0.015% $H_2O_2$ in PBS). After a final wash in PBS and distilled water, the sections were counterstained with 20% diluted hematoxylin (Santa Cruz Biotechnology) for 1 minute, and dehydrated. Sections were examined at various magnifications using an Axio Imager microscope (Carl Zeiss MicroImaging, GmbH, Oberkochen, Germany). Images of normal tissues and lesions were captured and processed using Motic Images plus 2.0. Quantification of the comparative DAB staining was performed using the Histo-Quest sortware.

6. Measurement of Cell Viability

200 µl of the cultured cancer cells were seeded into a 96-well plate to have $5 \times 10^3$ cells/well, and cultured for 24 hours at a temperature of 37° C. in a wet incubator with carbon 5% and oxygen 95% supplied thereto. Then, an empty vector (pSilencer 4.1-CMV-neo vector, Ambion, USA) and shRNA specific to NAG-1 were added to the ovarian cancer cells, cultured for 48 hours, and treated for 48 hours with an anticancer drug, Taxol, according to the concentrations. 50 µl of MTT solution (1 mg/ml) in PBS was added to each well, and cultured again for 6 hours. After the formation of formazan was confirmed, the MTT solution was completely removed. To remove formazan formed on the bottom of the well, 200 µl of dimethyl sulfoxide (DMSO) was added. Afterwards, a micro plate reader (Molecular Devices, USA) was used to measure absorbance at 560 nm. Accordingly, the relative cell viability was calculated when cells that were not treated with an anticancer drug was considered as 100%.

<Example 1> NAG-1 Expression Relative to Ovarian Cancer Stages

Tissues of normal and lesion sites were collected from 9 to 11 ovarian patients with each stage, and reacted with NAG-1 specific antibodies (Santa Cruz, USA). Then, via DAB and Hematoxylin staining, the protein expression amount was identified and quantified using the Histo-Quest software. As a result, it was confirmed that NAG-1 was highly expressed at the lesion sites of the patients with stages I/II, III, and IV (FIG. 1). Since NAG-1 was highly expressed in ovarian cancer stage-1/2, and thus, can be used for early histological verification.

Meanwhile, via immunostaining, the NAG-1 expression levels of general ovarian cancer cells (A2780) and ovarian cancer stem cells (R182) were compared. As a result, it was confirmed that the ovarian cancer stem cells (R182) expressed NAG-1 at a certain level, whereas the general ovarian cancer cells (A2780) expressed NAG-1 at a low level (FIG. 2).

<Example 2> Association Between NAG-1 Expression and Survival Rate of Ovarian Cancer Patient It was also confirmed that the survival rate was reduced in the case of NAG-1 high expression, and more particularly, that non-survivors showed NAG-1 high expression among patients with metastasis and recurrence (FIGS. 3 and 4).

The survival rate of ovarian cancer is significantly decreased due to drug resistance particularly during recurrence. In this regard, in the case of NAG-1 high expression during treatment of a patient with recurrence, NAG-1 can serve as a diagnostic marker for establishing customized treatment strategies other than the existing anticancer drug treatment.

<Example 3> Effect of Reducing Resistance Against Anticancer Drug by Controlling NAG-1 in Ovarian Cancer Stem Cell To confirm resistance of ovarian cancer stem cells (R182) against an anticancer drug by NAG-1 regulation, 5*10^3 R182 cells were cultured in a 96-well plate for 24 hours. Then, an empty vector (pSilencer 4.1-CMV-neo vector, Ambion, USA) and shRNA specific to NAG-1 were added to the ovarian cancer stem cells, cultured for 48 hours, and treated for 48 hours with an anticancer drug, Taxol, according to the concentrations. The amount of living cells by antibiotics was confirmed by MTT assay. As a result, it was confirmed that, when the NAG-1 expression was inhibited by the shRNA specific to NAG-1, the resistance against the anticancer drug was reduced (FIG. 5).

By the treatment of ovarian cancer with an anticancer drug (Taxol), ovarian cancer cells die, but ovarian cancer stem cells did not die. The ovarian cancer stem cells can cause cancer again, and due to resistance against the anticancer drug, further treatment with the anticancer drug is no longer effective. In this regard, the inventors of the present invention confirmed that, although NAG-1 was expressed at a low level in the ovarian cancer cells other than the ovarian cancer stem cells, the NAG-1 expression increased particularly in the ovarian cancer stem cells, and also discovered that NAG-1, which increased expression thereof in the ovarian cancer stem cells, was involved in resistance against the anticancer drug. Therefore, it is determined that NAG-1 can be used as a target gene for effective tumor therapy, and the NAG-1 inhibitor can be used as an anticancer drug resistance adjuvant.

In conclusion, NAG-1, which is overexpressed in ovarian cancer patients and ovarian cancer stem cells having resistance against an anticancer drug, has been shown to play a key role in chronic inflammatory response and anticancer drug resistance through the NAG-1 protein regulation. In this regard, NAG-1 is suggested as a diagnostic and drug-resistance screening target gene for tumor therapy (FIG. 6).

The invention claimed is:

1. A method of inhibiting resistance against paclitaxel for an ovarian cancer stem cell of an ovarian cancer patient, the method comprising:

adding a short hairpin RNA (shRNA) of SEQ ID NO: 1 as an inhibitor of expression of NSAID-activated protein 1 (NAG-1) protein to the ovarian cancer stem cell of the ovarian cancer patient; and treating the ovarian cancer stem cell with only the paclitaxel, wherein an inhibition of NAG-1 expression in the ovarian cancer stem cell of the ovarian cancer patient inhibits the resistance against only the paclitaxel.

2. A method of providing information for diagnosis of prognosis of resistance against paclitaxel for an ovarian cancer stem cell of an ovarian cancer patient, the method comprising:

treating an ovarian cancer stem cell line with a short hairpin RNA (shRNA) of SEQ ID NO: 1 as an inhibitor of expression or activity of NAG-1 protein and only paclitaxel;

measuring a level of expression or activity of NSAID-activated protein 1 (NAG-1) protein in the treated ovarian cancer stem cell line;

comparing the measured level of expression or activity of NAG-1 protein with a control sample; and determining inhibition of resistance against the paclitaxel, when the measured level of expression or activity of NAG-1 protein is lower than that of the control group.

3. The method of claim 2, wherein the level of expression or activity of NAG-1 protein is measured by one selected from the group consisting of reverse transcription-polymerase chain reaction (RT-PCR), enzyme-linked immunosorbent assay (ELISA), immunohistochemistry, western blotting, and fluorescence-activated cell sorting (FACS).

* * * * *